United States Patent [19]

Hoskins

[11] Patent Number: 4,684,615

[45] Date of Patent: Aug. 4, 1987

[54] STABILIZED ISOENZYME CONTROL PRODUCTS

[75] Inventor: Michael K. Hoskins, Irvine, Calif.

[73] Assignee: Ciba Corning Diagnostics Corp., Medfield, Mass.

[21] Appl. No.: 913,117

[22] Filed: Sep. 29, 1986

Related U.S. Application Data

[63] Continuation of Ser. No. 501,213, Jun. 6, 1983, abandoned.

[51] Int. Cl.⁴ ............................................. G01N 31/00
[52] U.S. Cl. ........................................ 436/16; 436/18
[58] Field of Search ........................... 436/8–18; 435/4, 188; 252/408.1

[56] References Cited

U.S. PATENT DOCUMENTS

| | | | |
|---|---|---|---|
| 1,599,930 | 9/1926 | Takamine et al. | 435/188 |
| 1,855,592 | 4/1932 | Wallerstein | 435/188 |
| 3,515,642 | 6/1970 | Mima et al. | 435/188 |
| 3,523,871 | 8/1970 | Matsuoka | 435/188 |
| 3,761,420 | 9/1973 | Bogardus | 435/188 |
| 4,358,394 | 11/1982 | Crews et al. | 436/18 |
| 4,451,569 | 5/1984 | Kobayashi et al. | 435/188 |

FOREIGN PATENT DOCUMENTS

| | | | |
|---|---|---|---|
| 0068788 | 4/1982 | Japan | 435/188 |
| 0108020 | 7/1982 | Japan | 435/188 |
| 0081782 | 5/1983 | Japan | 435/188 |

Primary Examiner—Deborah L. Kyle
Assistant Examiner—T. J. Wallen
Attorney, Agent, or Firm—Brian D. Voyce; Daniel Reitenbach

[57] ABSTRACT

Isoenzyme control reagents and methods for making same stabilized by means of plexiform stabilizing means. The preferred plexiform stabilizing means is selected from the group consisting of monosaccharide and disaccharide reducing sugars. The most preferred isoenzyme control reagent comprises the isoenzyme of interest obtained from selected tissue, preclarified human sera, stabilizing cofactor, a chelating agent means, a weak nonphosphate buffer and lactose as the most preferred plexiform stabilizing means.

4 Claims, No Drawings

STABILIZED ISOENZYME CONTROL PRODUCTS

This is a continuation of application Ser. No. 501,213, filed June 6, 1983, abandoned.

FIELD OF THE INVENTION

This invention relates to stabilized control products useful in the clinical environment and in particular relates to stabilized isoenzyme control reagents including CK and LDH isoenzymes.

BACKGROUND OF THE INVENTION

This invention is related to a co-pending application entitled "Stabilized Multiparameter Control Product", Ser. No. 501,358, filed June 6, 1983 by the inventor hereof. That application is fully incorporated herein by reference.

Isoenzymes, or isozymes, as they are alternatively referred to, are enzymes in multiple forms which are capable of performing the same general function but at different rates. They are sufficiently different in chemical composition so that they are generally separable electrophoretically. One such isoenzyme, lactate dehydrogenase (LDH) is found in five electrophoretically distinct fractions. Each of these electrophoretic species of LDH is a tetramer consisting of two polypeptide chain units, H and M, present in different proportion: $H_4$, $MH_3$, $M_2H_2$, $HM_3$, and $M_4$. These five isoenzymes differ in catalytic activity (affinity for the substrate, pyruvate as measured by the Michaelis constant), amino acid composition, heat lability, and immunological responses. The two peptides H and M are coded by different genes. Thus the type of enzyme present is under genetic control and regulated by the conditions of the environment imposed upon the cell.

Similarly, creatinine kinase (CK) is another isoenzyme which contains subunits of either M's or B's and thus may be present as MM, BB, or MB. The MB form is clinically significant as an indicator of myocardial information, however, this form is unstable and tends to disassociate to reform the MM or BB types. It is an object to stabilize a control reagent having the MB form.

The various proportions or combinations of isoenzymes present in the tissue may be related to the specific requirements of the cell in question and is thus affected by such factors as the extent of differentiation and development of the cell, as well as the level and type of metabolism occurring within the cell. Accordingly, the distribution between the various forms of isoenzymes provides diagnostically significant data. For instance, LDH exhibits significant control over cellular glycolosis. Specifically, $MH_3$ and $H_4$ isoenzyme types predominant in tissues with purely aerobic or respiratory metabolism. Accordingly, they may be used as diagnostic tools in determining the condition of muscles such as the heart—particularly with CK isoenzymes, the brain, liver and other organs in the case of alanine aminotransferase (ALT) or aspartase aminotransferase (AST). Yet another isoenzyme of significance is alkaline phosphatase gammaglutamyl transpeptidase.

With such attention being placed on the determination of isoenzyme levels, particularly important in the case of cardiac critical care patients, it is axiomatic that adequate controls must be available in order to ensure the proper operation of manual and automated methods designed to determine these levels. Heretofore, such controls as were available, have been typically unstable due to the highly unstable nature of the enzymes themselves.

It is an object of the present invention to provide control reagents having the necessary levels of isoenzymes present therein in a stabilized format.

It is another object of the present invention to provide methods whereby isoenzyme control reagents may be stabilized.

BRIEF SUMMARY OF THE INVENTION

In accordance with the objects and principles of the present invention, isoenzyme control reagents are provided for creatinine kinase, lactate dehydrogenase, alanine aminotransferase and aspartase aminotransferase which are substantially stabilized by the addition of plexiform stabilizing means. The preferred plexiform stabilizing means is selected from the group consisting of maltose, mannitol, cellobiose and lactose with the latter most being the most preferred. The plexiform stabilizing means is advantageously provided in a final concentration range of about 2%–8% with the ideal concentration occurring at about 6%. The ideal isoenzyme control reagent will have substantially all water removed, such as by lyophilization, to assist in long term storage and stability.

As a result, the control reagent products of the present invention may be made to act and behave in a more similar fashion as those of a patient and indeed, the instant reagents are capable of being run on any of the three separation systems presently in use: column chromatography, and the immuno-based separation type systems.

DETAILED DESCRIPTION AND BEST MODE

As has been previously intimated, there has heretofore been great difficulty in stabilizing such an isoenzyme control reagent and in particular, stabilizing the various isoenzyme subunits such as the CK isoenzyme unit MB without deleteriously affecting other subunit components or the tests therefor. With the addition of the plexiform stabilizing means of the present invention, these isoenzymes and their subunit constituents have now been stabilized and may be maintained in solution for significantly greater periods of time than previously possible. In dry form, obtained with substantially all water has been removed such as by lyophilization, the stability period is increased to an even greater extent.

The addition of the plexiform stabilizing means of the present invention results in depression of the actual freezing point. Depression of the freezing point is generally associated with slower freezing rates, however, faster freezing of the product of the present invention has been observed. It would appear, however, that the plexiform stabilizing means when added to the material of the present product results in the loss of the eutectic point plateau thus actually increasing the freezing rate. Associated with this phenomenon is the observation that the cakes formed during freezing are uniformly crystalline, as opposed to the often occurring powder forms. This would imply that the plexiform stabilizing means is holding the constituents in a stable, three dimensional "crystalline" structure thereby assisting in the removal of water, the stabilization of the constituents themselves, as well as speeding the reconstitution of the lyophilized material. These and other complex interactions are more fully described in the co-pending application referred to earlier and for a fuller explanation, reference is made thereto.

In order to make the isoenzyme control reagents of the present invention, a specific human tissue was selected in accordance with the type of enzyme containing product to be produced. For instance, for the CK MB subunit, heart tissue is selected, for the CK MM enzyme subunit muscle tissue is employed while for the CK BB subunit brain tissue is used. Similarly, these and other tissues including non-human tissues may be used as the source material for the isoenzymes or their subunits in accordance with well-known knowledge.

The tissue is then treated by grinding etc. to a form suitable for isoenzyme isolation by either chromatography, electrophoresis or other immunologically based system in accordance with techniques well-known. The thusly isolated enzyme components may be added in diagnostically significant proportions to a preferably preclarified, human sera base. The human sera is advantageously clarified to remove lipids by either filtering, freezing, reconstituting and filtering or by the addition of silica compounds such as aerosil all of which are methods well-known.

It is then advantageous to add to this material, a stabilizing cofactor as may be necessary to assist in the maintenance of binding site activity. For instance, for the CK isoenzymes, sulfhydryl containing compounds such as glutathione or dithiotreotol or n-actyl-cysteine are useful. Further, the ideal product also includes chelating means for removing metallic ions, if present, which may interfere with enzyme activity. If the enzyme's activity is not affected by the presence of metallic ions, this agent need not be included. Similarly, if no metallic ions are present this agent may again be eliminated. An example of such a chelating agent is ethylenediamine tetraacetic acid (EDTA).

Lastly, the isoenzyme product of the present invention will further comprise a weak, nonphosphate buffer. It is preferred that a nonphosphate buffer is employed in order to avoid phosphorus containing compounds which may otherwise interfere with some of the reactions, particularly those involving the adenine triphosphate (ATP) cycles. The buffer should be "weak" i.e. within the range of about 10–200 millimolar concentration. The pH of the buffer should ideally be selected or adjusted in order to preferably optimize activity and maximize stability. For instance, with the CK and LDH isoenzymes, a pH of approximately 7 is advantageous while the ideal pH for the alkaline phosphatase isoenzyme is in the range of about 7.6 to 7.8.

Finally, plexiform stabilizing means is added in order to provide the stability and other aforementioned advantages described herein or incorporated by reference. Such a plexiform stabilizing means is selected from the group consisting of monosaccharide and disaccharide reducing sugars and preferably will be selected from the group consisting of mannitol, maltose, cellobiose and lactose. As described in the referenced application, the most preferred, in terms of stability advantages and economic considerations, is lactose. The inventor hereof has found it desirable to present the plexiform stabilizing means in a final concentration range of about 2%–8% with the most preferred embodiment comprising approximately 6%.

The plexiform stabilizing means not only retards the disassociation of isoenzymes whose subunits tend to disassociate rather easily, but it also stabilizes the isoenzyme's electrophoretic patterns. The concentration of the plexiform stabilizing means is selected to retain the enzyme activity even if the product is freeze dried and may be preferably optimized for maximum enzyme activity. If too little plexiform stabilizing means is incorporated into the final product, then insufficient protection is derived, however, it is undesirable to add too much plexiform stabilizing means which in high concentrations not only may precipitate out of solution but may also block the active site of the protein. Thus, high concentrations of the plexiform stabilizing means actually tend to reduce enzyme activity and are consequently avoided.

An example of increased stability is presented in accompanying Table 1. The data therein represents the activity of a CK isoenzyme control stored in aqueous form at 37° C. It compares the data observed with an unstabilized isoenzyme control against the stabilized isoenzyme control from day 0 to day 30. Still greater increases in stability may be expected at lower temperatures i.e. 5° storage as well as in lyophilized storage format.

It may be readily appreciated by those skilled in the art that various modifications and substitutions may be made to the constituents listed above without departing from the spirit or scope of the present invention.

TABLE 1

| | CK ISOENZYME CONTROL 37° C. WET STABILITY STUDY | |
|---|---|---|
| Day | Unstabilized CK | Stabilized CK |
| 0 | 984 | 945 |
| | 984 | 931 |
| 3 | 944 | 945 |
| | 944 | 956 |
| 5 | 981 | 918 |
| | 972 | 930 |
| 9 | 938 | 901 |
| | 942 | 672[1] |
| 12 | 961 | 942 |
| | 965 | 948 |
| 16 | 695 | 679 |
| | 702 | 670 |
| 30 | 403[2] | 466[2] |
| | 408[2] | 462[2] |

[1]short sample [2]1:2 dilution results

I claim:

1. A method of stabilizing an isoenzyme control reagent comprising adding to an aqueous solution containing the isoenzymes to be stabilized against disassociation or rearrangement of subunits a plexiform stabilizing means selected from the group consisting of reducing monosaccharide sugars and reducing disaccharide sugars, said plexiform stabilizing means present in the range of about 2% to 8% weight per volume.

2. The method as provided in claim 1 wherein the plexiform stabilizing means is selected from the group consisting of maltose, mannitol, cellobiose and lactose.

3. The method as provided in claim 1 wherein the plexiform stabilizing means is lactose.

4. The method as provided in claim 3 wherein the lactose is present in the final concentration of about 6%.

* * * * *